(12) United States Patent
Null, Jr. et al.

(10) Patent No.: US 9,061,238 B2
(45) Date of Patent: Jun. 23, 2015

(54) GAS CONCENTRATOR

(71) Applicant: Invacare Corporation, Elyria, OH (US)

(72) Inventors: William A. Null, Jr., West Salem, OH (US); Samuel J. Shelnutt, North Ridgeville, OH (US)

(73) Assignee: Invacare Corporation, Elyria, OH (US)

( * ) Notice: Subject to any disclaimer, the term of this patent is extended or adjusted under 35 U.S.C. 154(b) by 109 days.

(21) Appl. No.: 13/834,717

(22) Filed: Mar. 15, 2013

(65) Prior Publication Data

US 2014/0260991 A1 Sep. 18, 2014

(51) Int. Cl.
*B01D 53/04* (2006.01)
*A61M 16/10* (2006.01)

(52) U.S. Cl.
CPC ........... *B01D 53/0407* (2013.01); *A61M 16/10* (2013.01); *B01D 53/0415* (2013.01); *B01D 2253/108* (2013.01); *B01D 2256/12* (2013.01); *B01D 2257/102* (2013.01); *B01D 2257/502* (2013.01); *B01D 2257/504* (2013.01); *B01D 2257/80* (2013.01); *B01D 2259/402* (2013.01); *B01D 2259/4533* (2013.01); *B01D 2259/455* (2013.01); *A61M 16/101* (2014.02); *Y02C 10/08* (2013.01)

(58) Field of Classification Search
USPC ....................... 96/121, 147, 151; 55/490, 512; 128/205.27
See application file for complete search history.

(56) References Cited

U.S. PATENT DOCUMENTS

| | | | |
|---|---|---|---|
| 4,449,990 A | | 5/1984 | Tedford, Jr. |
| 5,403,387 A | * | 4/1995 | Flynn et al. ..................... 96/143 |
| 5,578,115 A | * | 11/1996 | Cole ................................ 96/121 |
| 5,827,354 A | * | 10/1998 | Krabiell et al. ..................... 95/96 |
| 5,906,672 A | | 5/1999 | Michaels et al. |
| 5,917,135 A | | 6/1999 | Michaels et al. |
| 5,988,165 A | | 11/1999 | Richey, II et al. |
| 6,120,685 A | * | 9/2000 | Carlson et al. ................. 210/232 |
| 6,440,188 B1 | * | 8/2002 | Clements et al. ............... 55/378 |
| 6,558,457 B1 | * | 5/2003 | Kolczyk ......................... 96/134 |
| 6,918,953 B2 | * | 7/2005 | Lomax et al. .................... 96/130 |
| 7,294,161 B2 | * | 11/2007 | Connor et al. .................. 55/498 |
| 7,510,601 B2 | * | 3/2009 | Whitley et al. ................. 96/121 |
| 7,763,102 B2 | * | 7/2010 | Lomax et al. ................... 96/121 |
| 7,875,105 B2 | | 1/2011 | Chambers et al. |
| 8,262,783 B2 | * | 9/2012 | Stoner et al. ..................... 96/108 |
| 8,282,717 B2 | | 10/2012 | Chambers et al. |
| 8,562,725 B2 | | 10/2013 | Chambers et al. |
| 8,668,767 B2 | | 3/2014 | Sprinkle et al. |
| 2005/0072426 A1 | * | 4/2005 | Deane et al. ............. 128/204.26 |
| 2007/0137487 A1 | | 6/2007 | Whitley et al. |
| 2009/0199522 A1 | * | 8/2009 | Hilberer ...................... 55/385.1 |

(Continued)

FOREIGN PATENT DOCUMENTS

DE 102010036382 B3 * 10/2011
JP 20101179763 A 6/2010

OTHER PUBLICATIONS

International Search Report from PCT/US2014/018476 dated Jun. 18, 2014.

*Primary Examiner* — Frank Lawrence
(74) *Attorney, Agent, or Firm* — Calfee, Halter & Griswold LLP

(57) ABSTRACT

Embodiments of oxygen concentrators having a sieve bed that includes a vessel containing a separation medium are disclosed. In one embodiment, the sieve bed vessel attaches to a chassis component using a press-fit configuration to lock and seal the sieve bed vessel to a chassis component.

22 Claims, 13 Drawing Sheets

(56) References Cited

U.S. PATENT DOCUMENTS

| | | |
|---|---|---|
| 2011/0315140 A1 | 12/2011 | Shuman |
| 2012/0192864 A1 | 8/2012 | Galbraith |
| 2012/0266883 A1 | 10/2012 | Taylor |
| 2014/0190348 A1 | 7/2014 | Richey et al. |

* cited by examiner

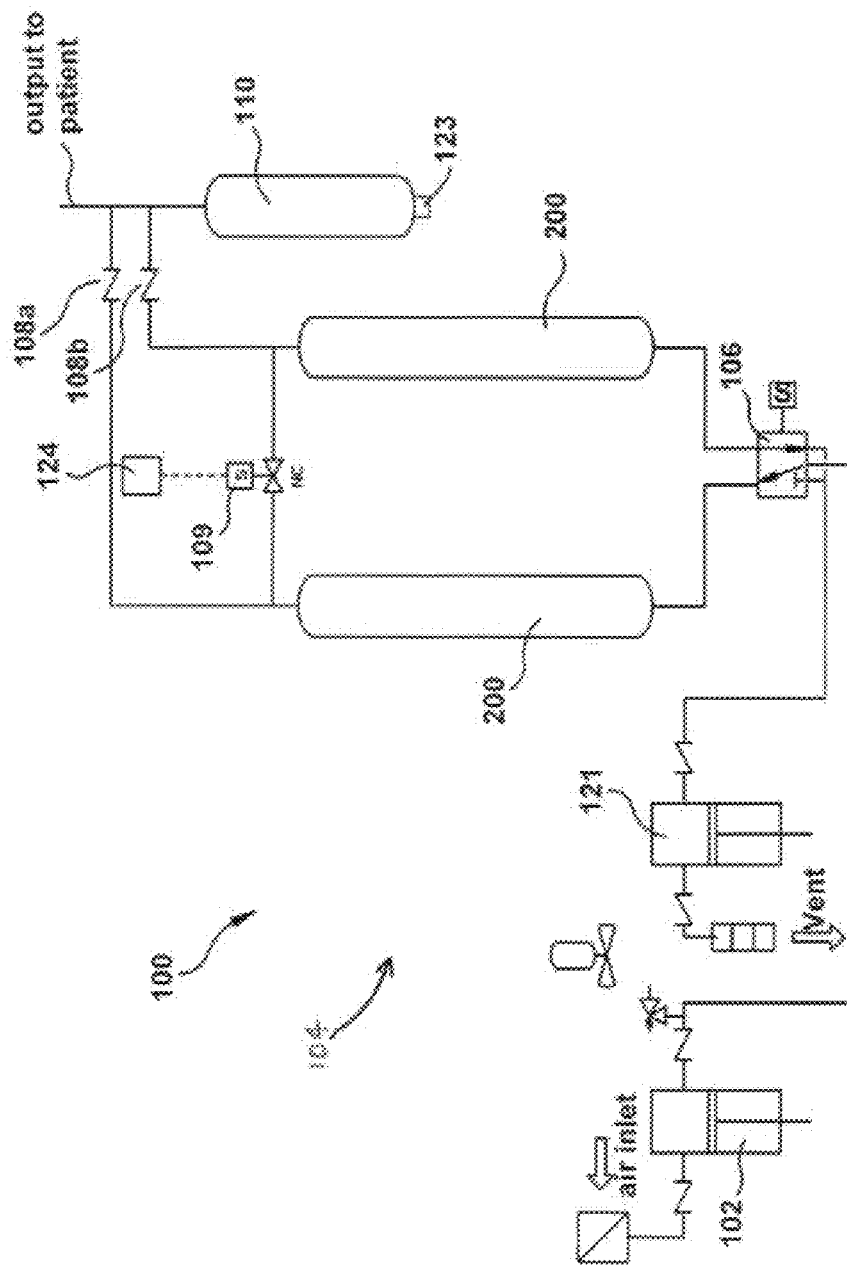

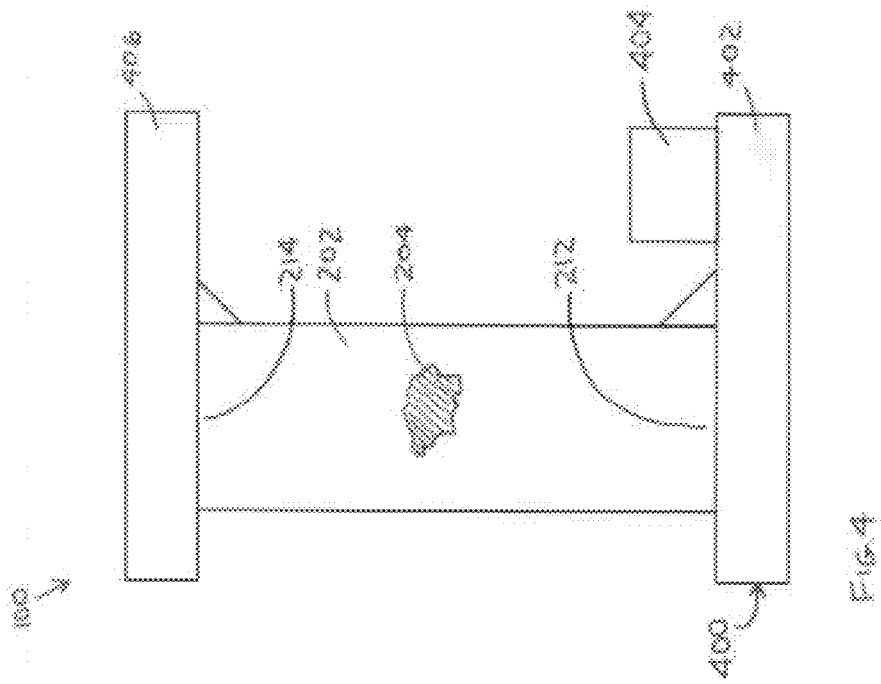
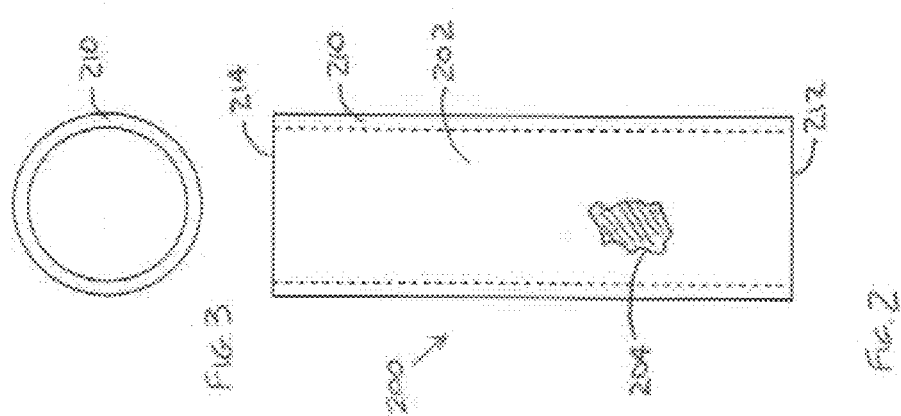

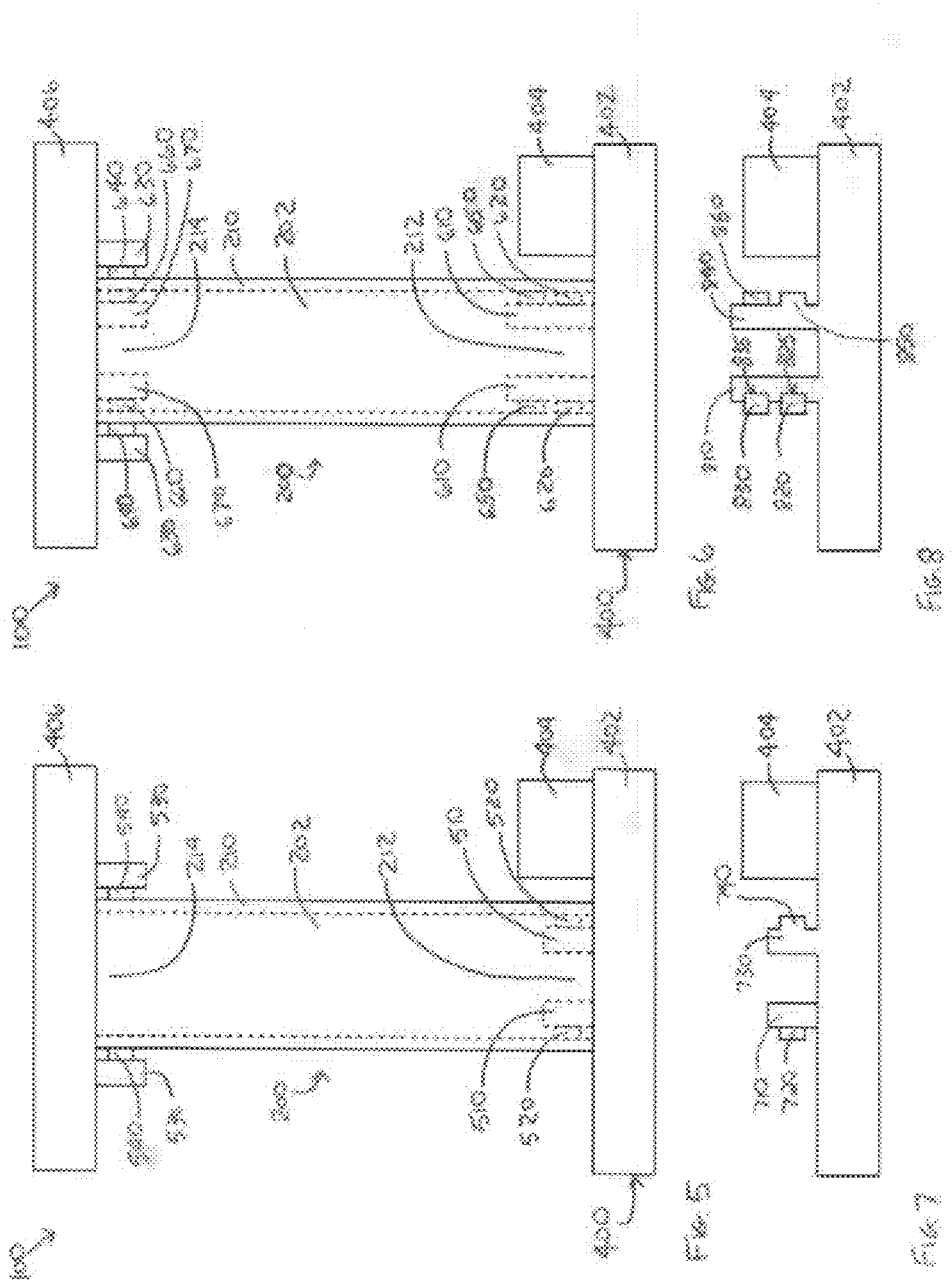

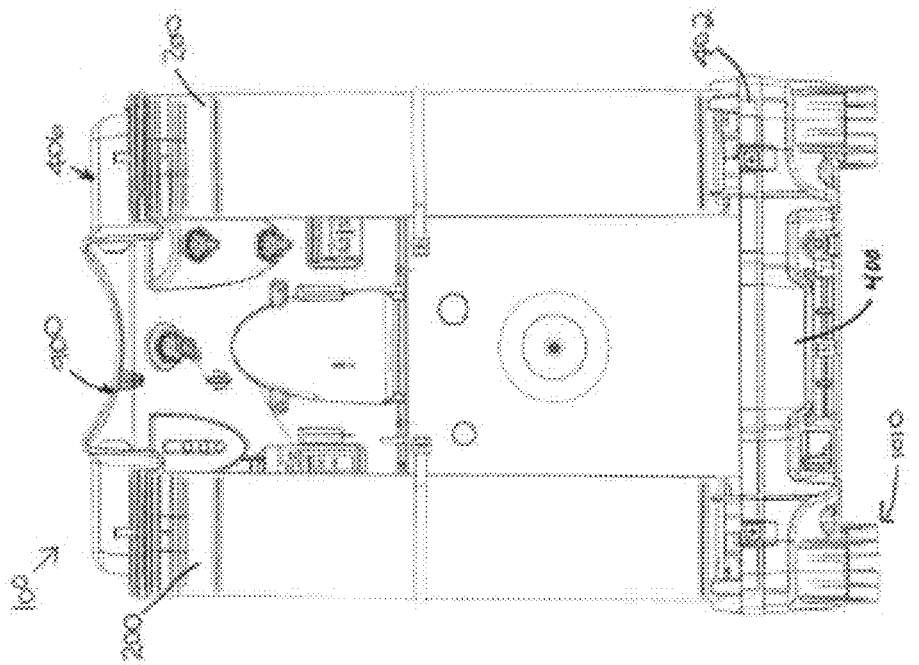
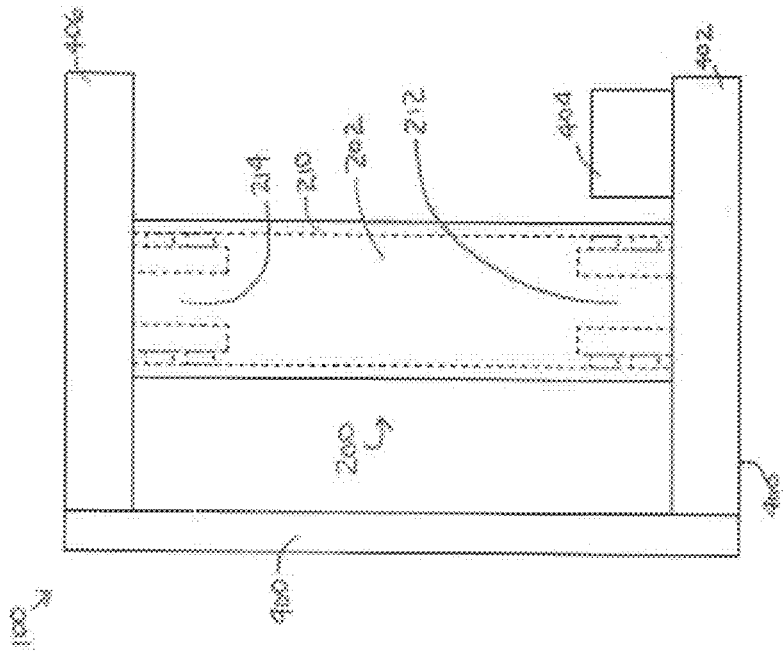

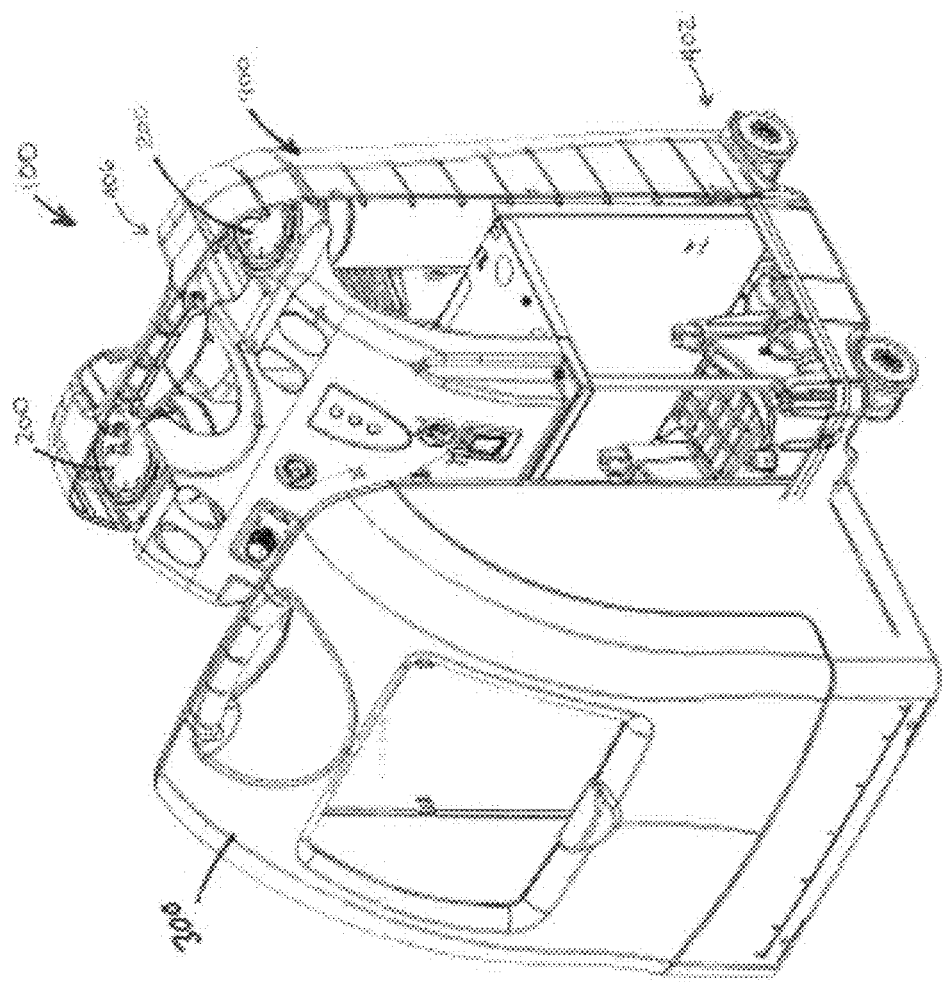

GAS CONCENTRATOR

BACKGROUND

Various applications exist for the separation of gaseous mixtures. For example, the separation of nitrogen from atmospheric air can provide a highly concentrated source of oxygen. These various applications include the provision of elevated concentrations of oxygen for medical patients and flight personnel. Hence, it is desirable to provide systems that separate gaseous mixtures to provide a concentrated product gas, such as a breathing gas with a concentration of oxygen.

Several existing product gas or oxygen concentrators, for example, are disclosed in U.S. Pat. Nos. 4,449,990, 5,906,672, 5,917,135, 5,988,165, 7,875,105, and 8,282,717 and U.S. patent application Ser. Nos. 12/106,861, 13/633,538, and 13/790,473, which are commonly assigned to Invacare Corporation of Elyria, Ohio and fully incorporated herein by reference.

SUMMARY

An concentrator for providing a breathing gas, including at least one sieve bed comprising a vessel containing a gas separation medium and a chassis component, including at least one vessel protrusion extending from the first chassis component to couple the at least one sieve bed vessel to the first chassis component, and a first locking element to lock the coupled vessel to the first chassis component.

The descriptions of the invention do not limit the words used in the claims in any way or the scope of the claims or invention. The words used in the claims have all of their full ordinary meanings.

BRIEF DESCRIPTION OF DRAWINGS

In the accompanying drawings, which are incorporated in and constitute a part of the specification, embodiments of the invention are illustrated, which, together with a general description of the invention given above, and the detailed description given below, serve to exemplify embodiments of this invention.

FIG. 1 is a schematic illustration of one embodiment of an oxygen concentrator;

FIG. 2 is a drawing of one embodiment of a sieve bed vessel;

FIG. 3 is a top view of the sieve bed vessel from FIG. 2;

FIG. 4 is a schematic drawing of one embodiment of a sieve bed vessel and two chassis components;

FIG. 5 is a schematic drawing of one embodiment of a sieve bed vessel attached to two chassis components;

FIG. 6 is a schematic drawing of one embodiment of a sieve bed vessel attached to and sealed with two chassis components;

FIG. 7 is a schematic drawing of one embodiment of a chassis component showing exemplary protrusions with locking features;

FIG. 8 is a schematic drawing of one embodiment of a chassis component showing exemplary protrusions with locking and sealing features;

FIG. 9 is a schematic drawing of one embodiment of a sieve bed vessel and two chassis components coupled together;

FIG. 10A is a drawing of one embodiment with two sieve bed vessels and two chassis components coupled together and supported by wheels;

FIG. 10B is a drawing of one embodiment of an oxygen concentrator with two sieve bed vessels and two chassis components coupled together and supported by wheels

DETAILED DESCRIPTION

Figure 11:
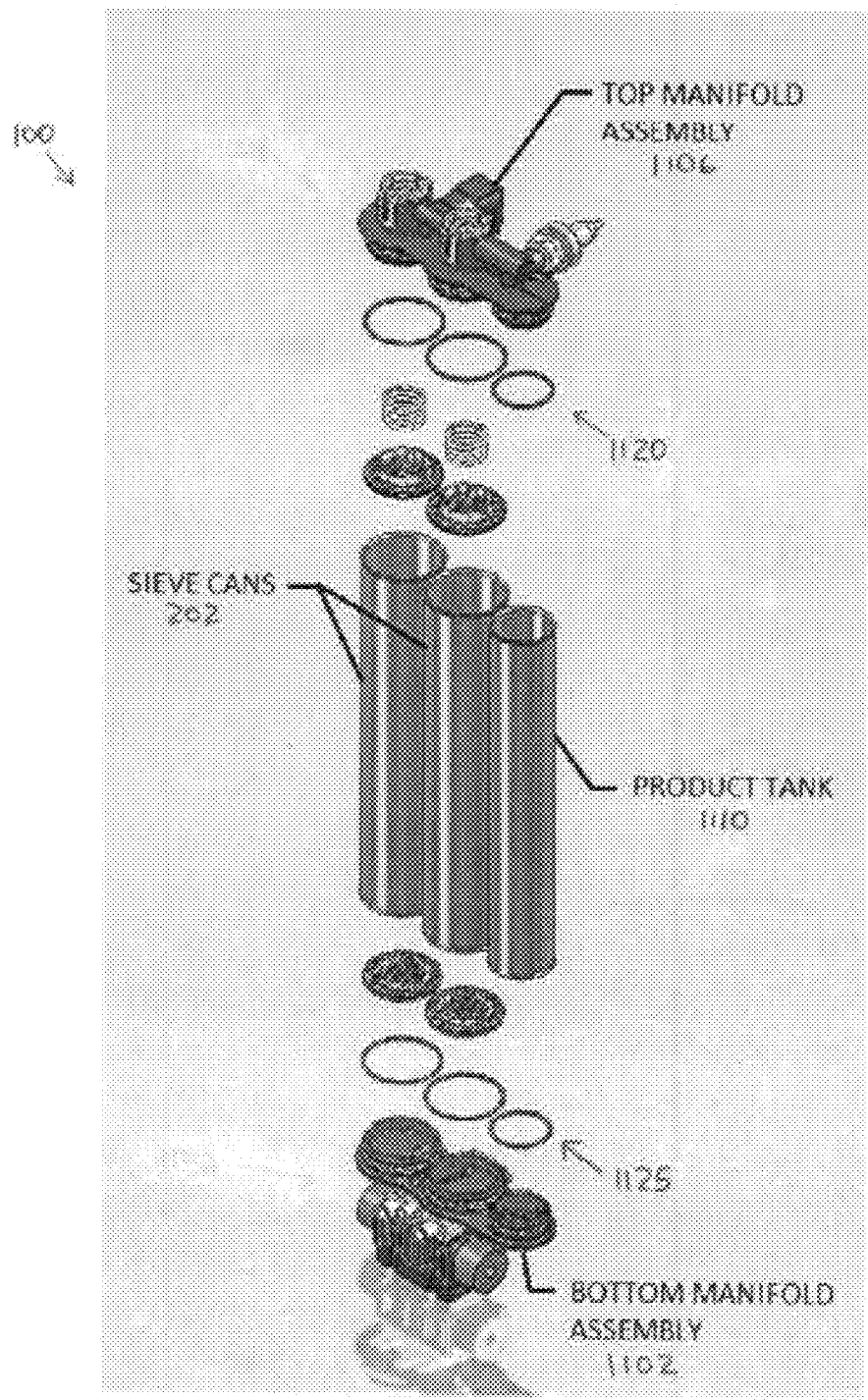
FIG. 11 illustrates one embodiment of an oxygen concentrator.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions—such as alternative materials, structures, configurations, methods, circuits, devices and components, software, hardware, control logic, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure, however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention, the inventions instead being set forth in the appended claims. Descriptions of exemplary methods or processes are not limited to inclusion of all steps as being required in all cases, nor is the order that the steps are presented to be construed as required or necessary unless expressly so stated.

Referring to FIG. 1, an exemplary gas concentrator 100 includes functional devices 104 that operate to concentrate gas, for example, oxygen from air. Some of the functional devices 104 have both functional components and structural components. For example, a sieve bed 200 includes a structural sieve bed vessel 202 that contains a functional sieve bed separation medium 204. (See also FIG. 2.) The functional devices 104 may be mounted or packaged in a chassis. In this application, "chassis components" are components that support and/or at least partially cover one or more of the functional devices 104 of the oxygen concentrator. In some embodiments, chassis components can incorporate or include functional devices or components. In one exemplary embodiment, a structural component of a functional device 104 of the oxygen concentrator 100 at least partially supports one chassis component of an oxygen concentrator with respect to another chassis component of the oxygen concentrator. For example, oxygen concentrators 100 with one or more sieve beds 200 that are used as structural components of a chassis 400 of the oxygen concentrator are disclosed herein. (See also FIG. 4.) The features described herein, either individually, in combination, or sub-combinations of the features can be implemented in a wide variety of different oxygen concentrators. The disclosed features can be used to mount a sieve bed in any oxygen concentrator, including but not limited to, the oxygen concentrators disclosed in U.S. Pat. Nos. 4,449,990, 5,906,672, 5,917,135, and 5,988,165, which are hereby fully incorporated by reference.

FIG. 1 illustrates the functional devices 104 of an exemplary oxygen concentrator 100 that may utilize the sieve beds 200 as structural components. The embodiment of the oxygen concentrator 100 shown in FIG. 1 includes two sieve beds 200. However, any number of sieve beds 200 can be used. For example, one sieve bed may be used, two sieve beds may be used, three sieve beds may be used, or more than three sieve beds may be used. Referring to FIGS. 2 and 3, each sieve bed includes a vessel 202 that contains a physical separation medium or material 204. The separation material 204 selectively adsorbs one or more adsorbable components of a gaseous mixture and passes one or more nonadsorbable components of the gaseous mixture through the vessel 202. The separation material 204 of one embodiment is a molecular sieve with pores of uniform size and essentially the same molecular dimensions. However, any separation material may be used. These pores selectively adsorb molecules in accordance with molecular shape, polarity, degree of saturation, and the like. In one embodiment, the physical separation medium is an aluminasilicate composition with 4 to 5 angstrom pores. More specifically, the molecular sieve, may be a sodium or calcium form of aluminasilicate, such as type 5A zeolite. Alternately, the aluminasilicate may have a higher silicon to aluminum ratio, larger pores, and an affinity for polar molecules, e.g. type 13× zeolite. The zeolites adsorb nitrogen, carbon monoxide, carbon dioxide, water vapor, and other significant components of air.

Referring to FIGS. 2 and 3, the sieve bed vessel 202 can take a wide variety of different forms. Any vessel capable of containing fluid under a pressure needed to force a gaseous mixture, such as air, through the separation medium 204 can be used. For example, the sieve bed vessel can be any vessel that can be pressurized to 20 to 30 psi. The sieve bed vessel 202 can be formed in a wide variety of different shapes and sizes. In the example illustrated by FIGS. 2 and 3, the sieve bed vessel 202 is cylindrical with a circular cross-section (FIG. 3). However, a cylindrical vessel can have any cross-section, such as, for example, oval, polygonal, etc. The sieve bed vessel 202 illustrated by FIGS. 2 and 3 has a cylindrical wall 210, a bottom end 212, and a top end 214. The vessel 202 can be made from a wide variety of different materials. Examples of materials that the vessel 202 can be made from include, but are not limited to, metals, such as aluminum, steel, and other alloys, plastics, and carbon fiber. Any material can be used that meets the pressure containment requirements of the sieve bed 200.

In the example illustrated by FIG. 1, a cross-over valving arrangement 106 selectively connects each one of the beds 200 with a source of the gas mixture, e.g. air under pressure, and the other bed with a negative pressure or vacuum. In one embodiment, the cross-over valving arrangement 106 selectively connects one of the beds 200 with an air pump or compressor 102 which supplies air under pressure and the other bed 200 with a vacuum pump 121 which draws a vacuum. The compressor 102 and vacuum pump 121 may be connected to a common drive motor. A solenoid or other cross-over valve actuating arrangement selectively causes the cross-over valving 106 to move alternately between first and second positions. In the first position, one sieve bed 200 is connected with the compressor 102 and the other sieve bed 200 is connected with the vacuum pump 121. In the second position, the connections of the sieve beds 200 to the compressor 102 and the vacuum 121 are switched.

As the gas mixture is introduced under pressure through a bed inlet to an adsorbed gas-free or regenerated bed 200, an adsorption zone of finite, relatively large size is formed. This adsorption zone is a region of the bed 200 in which the full capacity of the adsorbent 204 to hold the adsorbable components has not been reached. The composition of the gas in the voids of the zeolite varies from substantially pure primary product gas at the outlet end to the ambient gaseous mixture composition at the inlet end. This adsorption zone moves from the bed inlet toward a bed outlet with a velocity significantly less than the superficial gas velocity in the bed 200 and is dependent on the input gas pressure. When the adsorption zone reaches the outlet end of the bed 200, adsorbable components begin to flow through the bed outlet into the nonadsorbable primary product stream. This time is hereinafter referred to as the "breakthrough time". When breakthrough occurs, primary product enriched bed gas in the zeolite voids varies from a higher primary product gas concentration at the bed outlet to a lower concentration at the bed inlet. In the preferred embodiment the primary product enriched bed gas is about 80 percent primary product at breakthrough. While adsorption is occurring in one bed 200, the adsorbable components adsorbed by the separation medium 204 of the other bed 200 are purged or removed under vacuum in an exemplary embodiment.

In the example illustrated by FIG. 1, one sieve bed 200 is connected with a product tank 110 by way of a first check valve 108a or other unidirectional valving means. The first check valve 108a permits the primary product gas from the first sieve bed 200 to flow into the product tank 110 when product gas pressure in the first bed 200 exceeds the pressure of product gas in the product tank 110. The first check valve 108a prohibits the product gas from flowing from the product tank 110 back into the sieve bed 200. The second sieve bed 200 is connected with the product tank 110 by way of a second check valve 108b or other unidirectional valving means. The second check valve 108b again provides for unidirectional flow of the primary product gas from the second bed 200 to the product tank 110.

In the example illustrated by FIG. 1, a pressure equalization flow path extends between a pair of outlets of the first and second sieve beds 200. The flow path has a sufficient gas flow capacity such that when one bed 200 is under full pressure and the other bed 200 is under full vacuum, gas flow through the pressure equalization path substantially equalizes the bed pressures. In one embodiment, the flow path capacity is sufficient to bring the beds 200 into pressure equilibrium in about 3 percent of the cycle duration or about 2 seconds. A pressure equalization valve 109 selectively permits and prevents a gas flow through the flow path between the first and second sieve beds 200. A timing and control means 124, which can be microprocessor-based, cyclically causes the cross-over valve actuating means 106 and the pressure equalization valve 109 to be operated. The timing and control means 124 includes a clocking means that periodically and cyclically enables a cross-over valve control and a pressure equalization valve control.

Referring again to FIG. 1, the product tank 110 can maintain a reservoir of oxygen. The product tank 110 or an output of the product tank 110 can be monitored by a pressure transducer 123. FIG. 1 illustrates one of the wide variety of oxygen concentrator arrangements that can use one, two, or more sieve bed vessels 200 as structural components. Sieve beds vessels 200 can be used as structural members of any oxygen concentrator 100. Additional embodiments are disclosed in U.S. Pat. Nos. 4,449,990, 5,906,672, 5,917,135, 5,988,165, 7,875,105, and 8,282,717 and U.S. patent application Ser. Nos. 12/106,861, 13/633,538, and 13/790,473, which are hereby fully incorporated by reference.

FIG. 1 is a schematic illustration that shows one example of how functional devices 104 are interconnected in a way that facilitates concentration of oxygen from air. These functional devices 104 are mounted or packaged in a chassis that houses the functional devices. The chassis may be configured in a wide variety of ways. Any chassis configuration that supports and houses the functional devices 104, may be used. FIG. 4 illustrates an oxygen concentrator 100 that includes a chassis 400. The chassis 400 includes a first or base chassis component 402 and a second or cover chassis component 406 disposed over at least a portion of the functional components 104 in an exemplary embodiment. Other functional components 404 may also mount to chassis components 402, 406. The chassis 400 may include any number of chassis components and/or functional devices 104, including, for example, flow paths, valves, valve attachments, pumps, pump attachments, sensors, sensor attachments, seals, retainers, caps, etc.

The chassis 400 can also support any number of chassis components and/or functional devices 104, including at least one sieve bed 200. In this embodiment, the sieve bed vessel 202 is assembled as a structural component that supports the chassis component 406 with respect to the chassis component 402. In one embodiment, the sieve bed vessel 202 is coupled to the chassis component 402 at end 212 and to the chassis component 406 at end 214. The sieve bed vessel 202 can be coupled to the chassis component 402 and to the chassis component 406 in a wide variety of different ways, including a "press-together" or "press-fit" configuration, described in more detail below. The sieve bed vessel 202 can be coupled to the chassis components 402, 406 in any way, including those that cause the sieve bed vessel 202 to support the chassis component 406 with respect to the chassis component 402. In addition to a "press-together" or "press-fit" configuration, other exemplary ways that the sieve bed vessel 202 can be coupled to one or more chassis components include, but are not limited to, attachment with mechanical fasteners, gluing, welding, threaded engagement between the vessel and a chassis component, and configuring a chassis component to fit onto a portion of the sieve bed vessel 202. Any of these attachment techniques may be used in combination with each other, including at the same end 212, 214 of the sieve bed vessel 202, or at different ends 212, 214 of the sieve bed vessel 202.

FIG. 5 illustrates an exemplary oxygen concentrator arrangement 100 where a protrusion 510 extends from the chassis component 402. The end portion 212 of the sieve bed vessel 202 is positioned over the protrusion 510 to couple (e.g., engage and/or attach) the end portion 212 to the chassis component 402. In this embodiment, a locking element or feature 520 also extends between the protrusion 510 and the sieve bed vessel wall 210. The locking feature 520 engages the inner surface of the sieve bed wall 210 and the outer surface of the protrusion 510 as the sieve bed vessel 202 is positioned over the protrusion 510, locking the sieve bed vessel 202 to the chassis component 402 in a "press-fit" or "press-together" configuration. The locking feature 520 may be configured in any orientation that captures the sieve bed wall 210 and the protrusion 510 as the sieve bed wall 210 mates to the chassis component 402. In the example illustrated by FIG. 5, the protrusion 510 is generally parallel to the sieve bed vessel 202 and sieve bed wall 210. The locking feature 520 may be configured to prevent removal of the sieve bed vessel 202 once the sieve bed vessel 202 is positioned or "pressed" over the protrusion 510. In this manner, the protrusion 510 and the locking feature 520 act as a "one-way" assembly device. In various embodiments, the locking feature may be integrated with or attached to the sieve bed wall 210 and/or the protrusion 510.

In one embodiment, the protrusion 510 may be a ridge extending from the chassis component 402 that matches the cross sectional shape of the sieve bed vessel 202, such as, for example, a circular ridge that interfaces with a sieve bed vessel 202 with a circular cross section. In another embodiment, the protrusion 510 may be a series of protrusions 510 extending from the chassis component 402 in a matching cross sectional arrangement. In other embodiments, the locking feature 520 may be a continuous feature throughout the entire protrusion 510 or may be a series of locking features 520 distributed along the protrusion 510. In another embodiment, the locking feature may be formed into the sieve bed wall 210. In other embodiments, the protrusion 510 and/or locking feature 520 may also provide a seal between the sieve bed vessel 202 and the chassis component 402. In other embodiments, the chassis component 402 includes a sealing feature or component that seals the end portion 212 to the chassis component 402 when the sieve bed vessel 202 is mated to the chassis component 402.

FIG. 5 also shows a protrusion 530 that extends from the chassis component 406. The end portion 214 of the sieve bed vessel 202 is positioned inside of the protrusion 530 to couple the end portion 214 to the chassis component 406. In this embodiment, a locking element or feature 540 also extends between the protrusion 530 and the sieve bed vessel wall 210. The locking feature 540 engages the outer surface of the sieve bed wall 210 and the inner surface of the protrusion 530 as the sieve bed vessel 202 is positioned inside of the protrusion 530, locking the sieve bed vessel 202 to the chassis component 406 in a "press-fit" or "press-together" configuration. The locking feature 540 may be configured in any orientation that captures the sieve bed wall 210 and the protrusion 530 as the sieve bed wall 210 mates to the chassis component 406. In the example illustrated by FIG. 5, the protrusion 530 is generally parallel to the sieve bed vessel 202 and sieve bed wall 210. The locking feature 540 may be configured to prevent removal of the sieve bed vessel 202 once the sieve bed vessel 202 is positioned inside of the protrusion 530. In this manner, the protrusion 530 and locking feature 540 also act as a "one-way" assembly device. In various embodiments, the locking feature may be integrated with or attached to the sieve bed wall 210 and/or the protrusion 530

In one embodiment, the protrusion 530 may be a ridge extending from the chassis component 406 that matches the cross sectional shape of the sieve bed vessel 202, such as, for example, a circular ridge that interfaces with a sieve bed vessel 202 with a circular cross section. In another embodiment, the protrusion 530 may be a series of protrusions 530 extending from the chassis component 406 in a matching cross sectional arrangement. In other embodiments, the locking feature 540 may be a continuous feature throughout the entire protrusion 530 or may be a series of locking features 540 distributed along the protrusion 530. In another embodiment, the locking feature may be formed into the sieve bed wall 210. In other embodiments, the protrusion 530 and/or locking feature 540 may also provide a seal between the sieve bed vessel 202 and the chassis component 406. In other embodiments, the chassis component 406 includes a sealing feature or component that seals the end portion 214 to the chassis component 406 when the sieve bed vessel 202 is mated to the chassis component 406.

FIG. 6 illustrates another exemplary oxygen concentrator arrangement 100 where a protrusion 610 extends from the chassis component 402. The end portion 212 of the sieve bed vessel 202 is positioned over the protrusion 610 to couple the end portion 212 to the chassis component 402. In this embodiment, a locking feature 620 also extends between the protrusion 610 and the sieve bed vessel wall 210. The locking feature 620 engages the inner surface of the sieve bed wall 210 and the outer surface of the protrusion 610 as the sieve bed vessel 202 is positioned over the protrusion 610, locking the sieve bed vessel 202 to the chassis component 402 in a "press-fit" or "press-together" configuration, similar to protrusion 510 and locking feature 520. However, in this embodiment, a sealing element 650 may also extend between the protrusion 610 and the sieve bed vessel wall 210 to provide a seal between the inner surface of the sieve bed wall 210 of the sieve bed vessel 202 and the chassis component 402.

In one embodiment, protrusion 610 may be a ridge extending from the chassis component 402 that matches the cross sectional shape of the sieve bed vessel 202. In this embodiment, the sealing element 650 may also match the cross sectional shape of the sieve bed vessel 202. Likewise, the locking feature 620 may be a continuous feature throughout the entire protrusion 610 or may be a series of locking features 620 distributed along the protrusion 610.

FIG. 6 also shows a protrusion 630 that extends from the chassis component 406. The end portion 214 of the sieve bed vessel 202 is positioned inside of the protrusion 630 to couple the end portion 214 to the chassis component 406. In this embodiment, a locking feature 640 also extends between the protrusion 630 and the sieve bed vessel wall 210. The locking feature 640 engages the outer surface of the sieve bed wall 210 and the inner surface of the protrusion 630 as the sieve bed vessel 202 is positioned inside of the protrusion 630, locking the sieve bed vessel 202 to the chassis component 406 in a "press-fit" or "press-together" configuration, similar to protrusion 530 and locking feature 540. However, in this embodiment, a sealing element 660 may provide a seal between the inner surface of the sieve bed wall 210 and the chassis component 406. As shown in this embodiment, the sealing element may extend from a protrusion 670 that extends from the chassis component 406. In this embodiment, the end portion 214 of the sieve bed vessel 202 is positioned inside of the protrusion 630 and outside of the protrusion 670 to attach and seal the end portion 214 to the chassis component 406.

As in the embodiments above, protrusions 630, 670 may be a ridge extending from the chassis component 406 that matches the cross sectional shape of the sieve bed vessel 202. In one embodiment, the sealing element 660 may also match the cross sectional shape of the sieve bed vessel 202. Likewise, the locking feature 640 may be a continuous feature throughout the entire protrusion 630 or may be a series of locking features 640 distributed along the protrusion 630.

Although FIGS. 5 and 6 show various combinations of embodiments of attaching the sieve bed vessel 202 to the chassis components 402, 406, any of these embodiments may be used for attaching both ends 212, 214 of the sieve bed vessel 202 to other components, including, for example, chassis components 402, 406. In other embodiments, any combination of the various embodiments may be used together for attaching one or both ends 212, 214 of the sieve bed vessel 202 to other components.

FIGS. 7 and 8 show various exemplary protrusions, locking features, and sealing elements, which also can be used in any combination with any of the above embodiments. For example, FIG. 7 shows a protrusion 710 that is attached to the chassis component 402 as a separate component. Generally, different components may be attached to each other in any acceptable manner, including, for example, friction fit, press fit, mechanical fasteners, gluing, welding, threaded engagement, etc. These attachment schemes include temporary attachments that are not complete, for example, until another component engages the component. Locking feature 720 is also attached to the protrusion 710 as a separate component. FIG. 7 also shows a protrusion 730 with an integrally formed, e.g., molded, locking feature 740 and where the protrusion 730 is integrally formed into the chassis component 402.

FIG. 8 shows a protrusion 810 integrated into the chassis component 402, but with locking feature 820 and sealing element 830 attached to the protrusion 810 as separate components. In this embodiment, protrusion 810 includes a recess 825 for the locking feature 820 to fit into and a recess 835 for the sealing element 830 to fit into. These components 820, 830 may be loosely affixed to the protrusion 810 until the sieve bed vessel is installed over the protrusion 810, for example, to press the locking feature 820 and sealing element 830 between the inner surface of the sieve bed wall 210 and the protrusion 810. For example, while "pressing" the sieve bed wall 210 over the protrusion 810, the sealing element 830 may be compressed between the inner surface of the sieve bed wall 210 and the protrusion 810, providing an air-tight seal. Similarly, while "pressing" the sieve bed wall 210 over the protrusion 810, the locking feature 820 may be compressed or deformed between the inner surface of the sieve bed wall 210 and the protrusion 810, thereby "locking" the vessel 202 to the chassis component 402 by creating a "high-friction" interface that would require a relatively high removal force.

Protrusion 840 is shown with an integrated locking feature 850 and where the protrusion 840 is integrally formed into the chassis component 402. Sealing feature 860 is attached to the protrusion 840 as a separate component. It should be appreciated that there are many other combinations of these features that may be used for attaching one or both ends 212, 214 of the sieve bed vessel 202 to other components, such as, for example, chassis components 402, 406.

FIG. 9 illustrates an embodiment similar to the embodiment of FIG. 6 where first chassis component 402 and the second chassis component 406 are coupled together. The coupling of the chassis components 402, 406 captures the sieve bed vessel 202 between the chassis components at ends 212, 214, including, for example, via the "press-fit" configuration described above. The chassis components 402, 406 may be coupled together in a wide variety of different ways. The chassis components may be coupled directly together or the chassis components may be coupled together by one or more intermediate components 900 as illustrated by FIG. 9. The chassis components may be coupled together in any way that the position of the chassis component 406 is fixed relative to the chassis component 402. In the embodiment illustrated by FIG. 9, the sieve bed vessel 202 is captured between the chassis components and supports the chassis component 406 with respect to the chassis component 402.

FIG. 10A is a drawing of an oxygen concentrator 100 embodiment similar to the embodiment of FIG. 9 where a first chassis component 402 and a second chassis component 406 are coupled together by one or more intermediate components 900 and the first chassis component 402 is supported by optional wheels 1010 that allow the oxygen concentrator 100 to be moved more easily. FIG. 10B is another drawing of an oxygen concentrator 100 embodiment similar to the embodiment of FIG. 9 and FIG. 10, and also showing front housing or cover 300.

FIGS. 11-14 illustrate an exemplary oxygen concentrator 100 utilizing an exemplary protrusion similar to protrusion 810, as shown in FIG. 8. As shown in FIG. 11, the concentrator 100 includes two sieve bed cans or vessels 202 and exemplary chassis components, such as, for example, an exemplary bottom manifold assembly 1102 and an exemplary top manifold assembly 1106. An exemplary product tank 1110 is also shown, which may have a configuration similar to the sieve bed vessels 202. Manifold assemblies 1102, 1106 may include various functional devices 104, as described above, including, for example, flow paths, valves, valve attachments, pumps, pump attachments, sensors, sensor attachments, seals, retainers, caps, etc. FIG. 11 also shows other components, for example, that may be installed into the sieve bed vessels 202 or the manifold assemblies 1102, 1106 before or while the manifold assemblies 1102, 1106 are coupled to the sieve bed vessels 202. FIG. 11 also shows exemplary locking features, shown as retaining rings 1120, for locking the ends of the sieve bed vessels 202 and the product tank 1110 to the manifold assemblies 1102, 1106.

Figure 12:
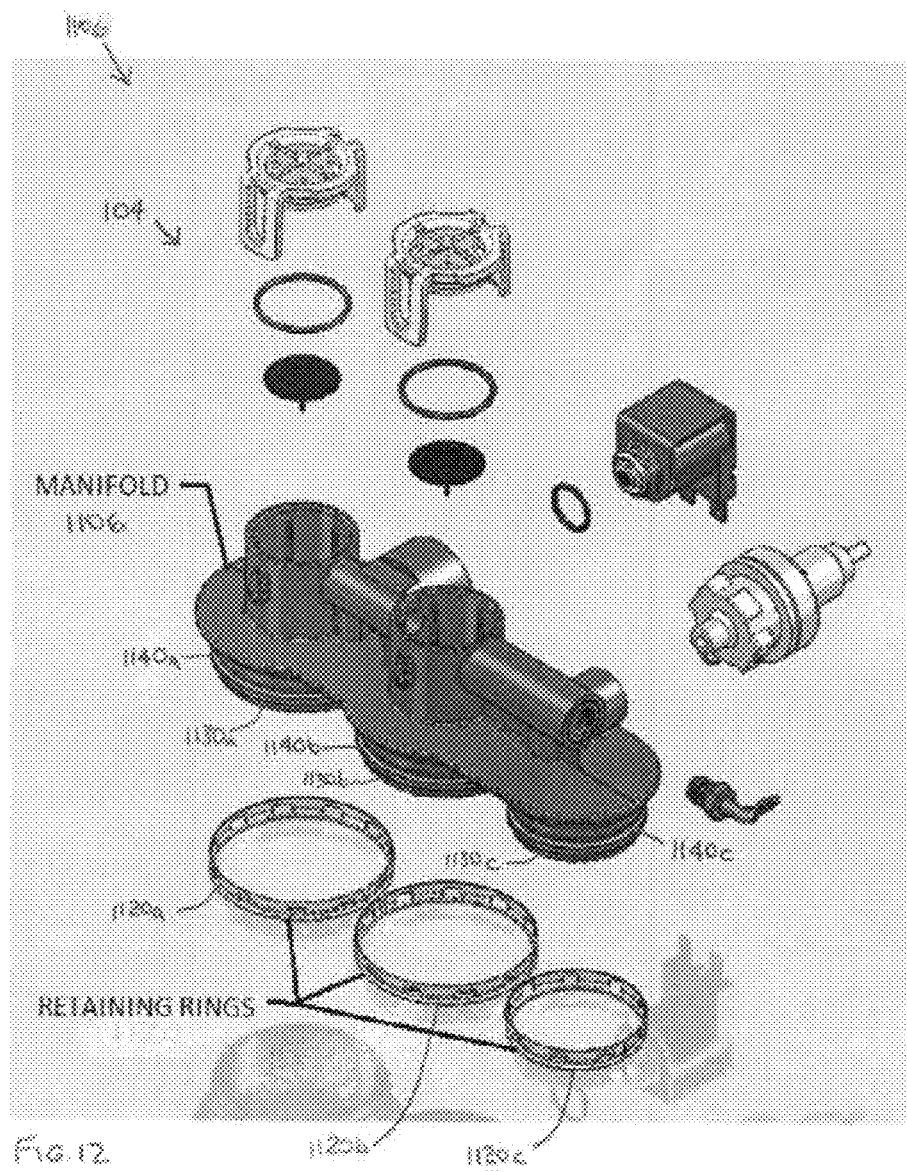
FIG. 12 illustrates one embodiment of a top manifold assembly of an oxygen concentrator.

FIG. 12 is an exploded view of the top manifold assembly 1106 from FIG. 11, shown with and attaching to various functional devices 104. The manifold assembly 1106 is also shown with exemplary retaining rings 1120, protruding ridges 1130, and o-ring seals 1140. The "press-fit" or "press-together" coupling of these components can result in a structurally strong, non-removable, and air-tight seal between the sieve bed vessels 202 and the product tank 1110 to the manifold assembly 1106. The retaining rings 1120 lock the sieve bed vessels 202 and the product tank 1110 to the manifold assembly 1106 in a "press-fit" or "press-together" manner, as described above. The retaining rings 1120 may be configured in such a manner to prevent the sieve bed vessels 202 or the product tank 1110 from being removed from the manifold assembly 1106 after installation. The o-ring seals 1140 seal the inner surface of the sieve bed vessels 202 or the product tank 1110 to the manifold assembly 1106.

For example: retaining ring 1120a, protruding ridge 1130a, and o-ring seal 1140a may be used to couple the top end of a sieve bed vessel 202 to the manifold assembly 1106; retaining ring 1120b, protruding ridge 1130b, and o-ring seal 1140b may be used to couple the top end of another sieve bed vessel 202 to the manifold assembly 1106; and retaining ring 1120c, protruding ridge 1130c, and o-ring seal 1140c may be used to couple the top end of a product tank 1110 to the manifold assembly 1106. In this embodiment, the protruding ridge 1130 feature of the manifold assembly 1106 is molded as part of the manifold assembly 1106 from the same plastic material. In other embodiments, the protruding ridge 1130 may be insert molded with the manifold assembly 1106 or attached to the manifold assembly 1106. In this embodiment, the protruding ridge 1130 has recesses molded into the side of the protruding ridge 1130 to accept the retaining ring 1120 and o-ring seal 1140. As discussed in more detail below, the retaining ring 1120 is attached to the protruding ridge 1130 of the manifold assembly 1106 in a recess to maintain the position of the retaining ring 1120 on the manifold assembly 1106. Similarly, the o-ring seal 1140 is attached to the protruding ridge 1130 of the manifold assembly 1106 in a recess to maintain the position of the o-ring seal 1140 on the manifold assembly 1106.

Figure 13:
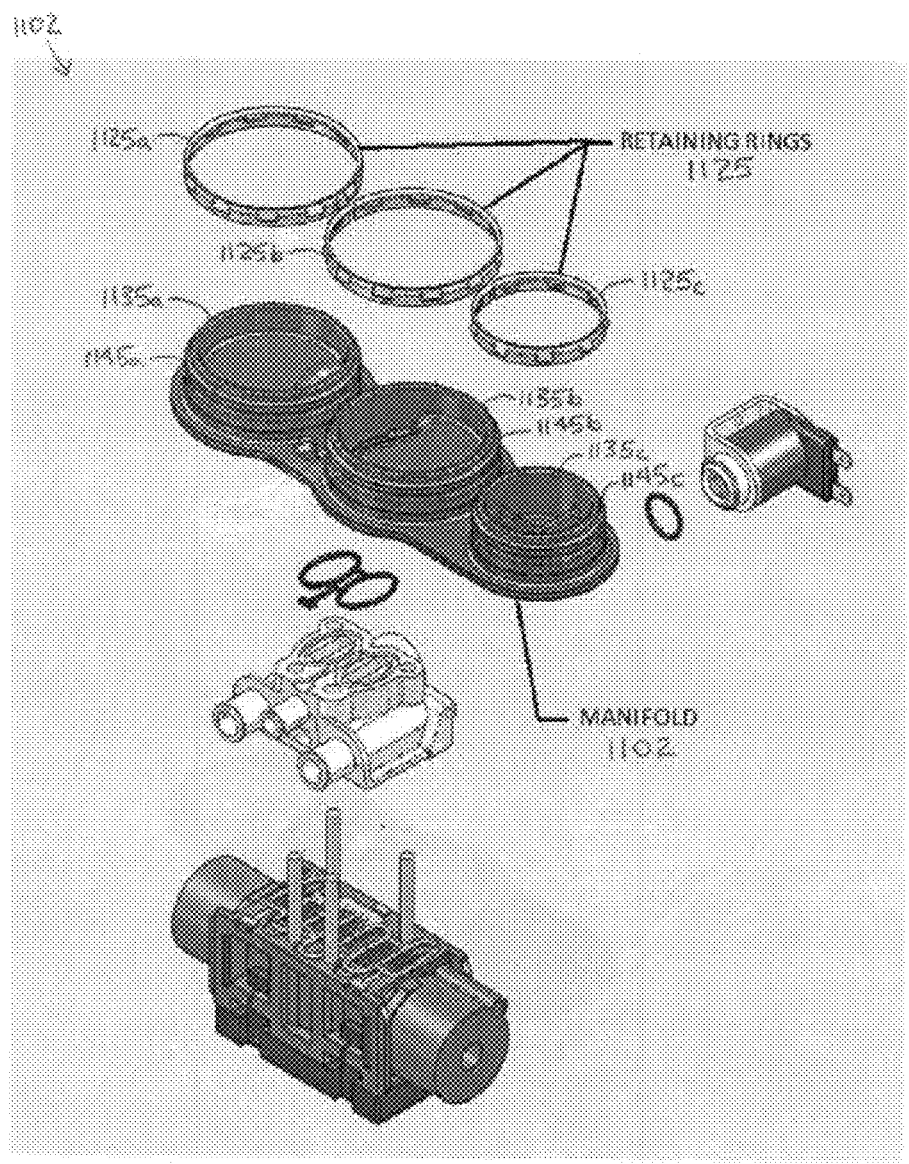
FIG. 13 illustrates one embodiment of a bottom manifold assembly of an oxygen concentrator.

FIG. 13 is an exploded view of the bottom manifold assembly 1102 from FIG. 11, shown with and attaching to various functional devices 104. The manifold assembly 1102 is also shown with exemplary retaining rings 1125, protruding ridges 1135, and o-ring seals 1145. The function and assembly of these components is similar to the retaining rings 1120, protruding ridges 1130, and o-ring seals 1140 discussed above in relation to the top manifold assembly 1106 in FIG. 12.

Figure 14:
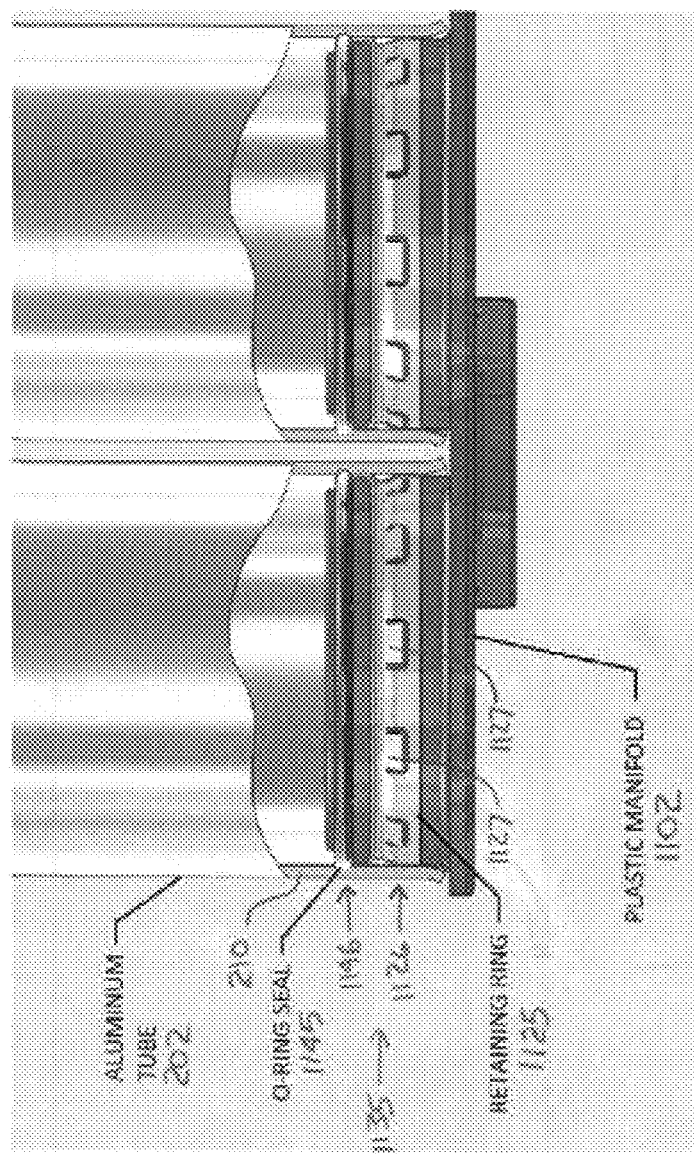
FIG. 14 illustrates one embodiment of two sieve bed vessels coupled to a bottom manifold assembly of an oxygen concentrator.

FIG. 14 is a further exploded view of the bottom manifold assembly 1102 from FIG. 11, shown coupling with the bottom end of exemplary sieve bed vessels 202. FIG. 14 shows the sieve bed vessels after they have been pressed onto the manifold assembly 1102. This embodiment is shown with exemplary retaining rings 1125, protruding ridges 1135, and o-ring seals 1145. In this embodiment, the protruding ridge 1135 has a recess 1126 molded into the side of the protruding ridge 1135 to accept the retaining ring 1125 and a recess 1146 molded into the side of the protruding ridge 1135 to accept the o-ring seal 1145. The retaining rings 1125 are shown with a plurality of tabs 1127 to lock the sieve bed vessels 202 to the manifold assembly 1102 during the "press-fit" or "press-together" assembly operation. In this embodiment, the tabs 1127 are stamped into the retaining rings 1125 and are biased or bent in the direction of assembly before installation of the sieve bed vessels 202 to the manifold assembly 1102. In this embodiment, as the vessel 202 is slid over the tabs 1127 of the retaining ring 1125 during the "press-fit" installation, the tabs 1127 are deformed towards the protruding ridge 1135, creating a high-friction interface. This configuration allows for a relatively low insertion force while the inner surface of the sieve bed wall 210 is pressed over the tabs 1127 during assembly. However, once the sieve bed vessels 202 are seated onto the manifold assembly 1102, the tabs resist removal of the sieve bed vessels 202 by locking into the inner surface of the sieve bed wall 210, establishing a relatively high removal force. In other embodiments, the configuration of the tabs 1127 may be of any quantity, spacing, geometry, etc. suitable for establishing the required insertion and removal force requirements of any particular application. The o-ring seals 1145 seal the inner surface of the sieve bed wall 210 to the manifold assembly 1102 during the "press-fit" assembly operation. In this embodiment, the o-ring seals 1145 make contact with the inner surface of the sieve bed wall 210 and the manifold assembly 1102 at the same time, which may include deforming and/or compressing.

Figure 15:
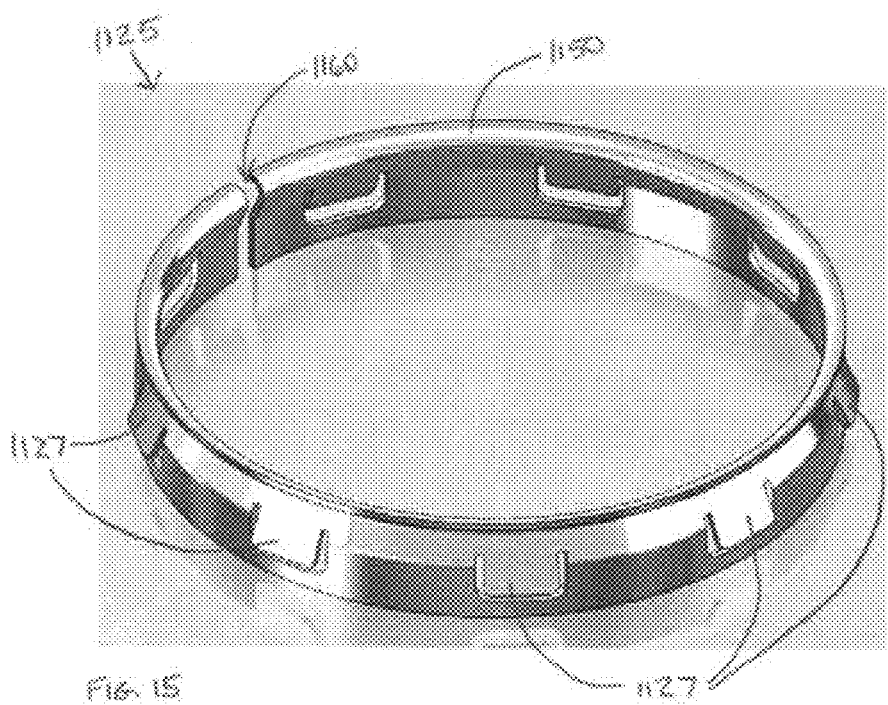
FIGS. 15-20 illustrate exemplary locking elements.

FIG. 15 is a view of an exemplary retaining ring 1125. In this embodiment, tabs 1127 are stamped into the retaining ring 1125 and are biased or bent in the direction of assembly. In other embodiments, tabs may be extending at a different angle relative to the ring 1125 or extending perpendicular to the ring 1125. The ring 1125 is also shown with an exemplary ridge 1150 for engaging with a recess 1126 of a protruding ridge 1135 (as shown in FIG. 14). The ring 1125 is also shown with an exemplary opening 1160 that may allow the ring 1125 to temporarily expand when engaging the protruding ridge 1135.

Figure 16:
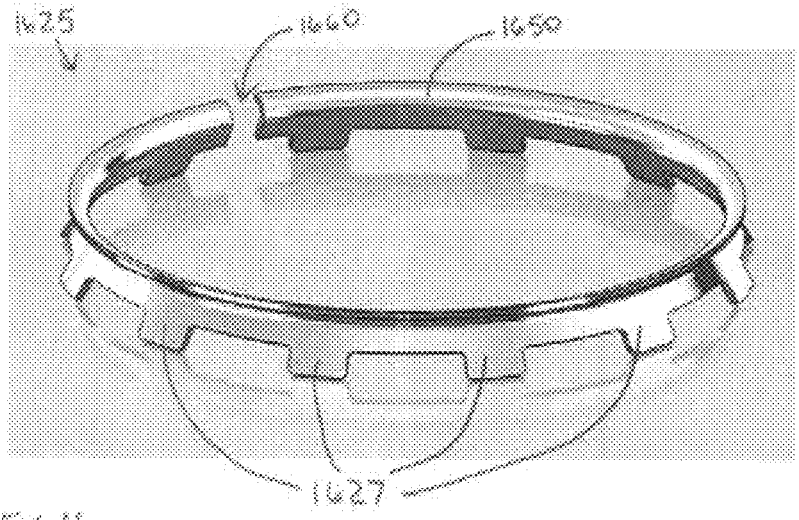

FIG. 16 is a view of another exemplary retaining ring 1625. In this embodiment, tabs 1627 are stamped into the retaining ring 1625 and are biased or bent in the direction of assembly. In this embodiment, the tabs 1627 are not surrounded by retaining ring 1625 material. The ring 1625 is also shown with an exemplary ridge 1650 for engaging with a recess of a protruding ridge of a chassis component. The ring 1625 is also shown with an exemplary opening 1660 that may allow the ring 1625 to temporarily expand when engaging the protruding ridge.

Figure 17:
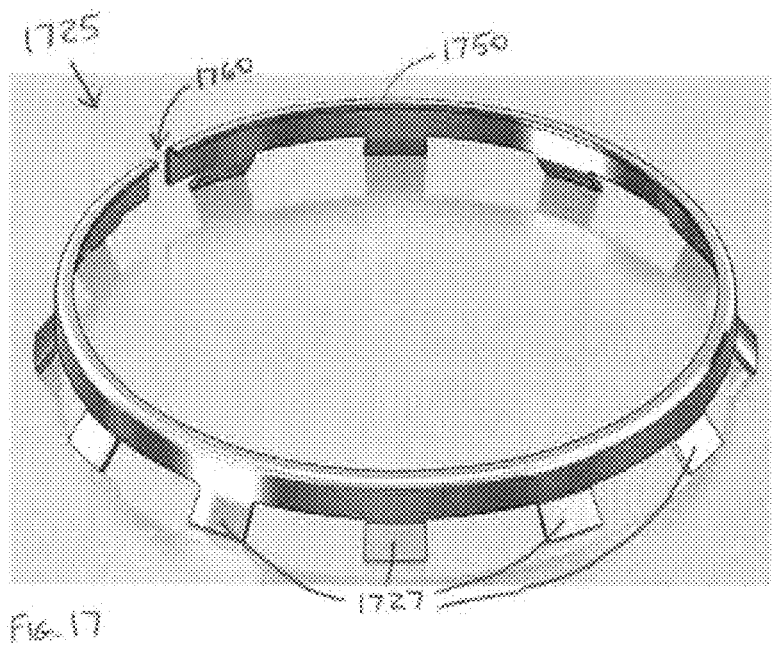

FIG. 17 is a view of another exemplary retaining ring 1725. In this embodiment, tabs 1727 are stamped into the retaining ring 1725 and are biased or bent in the direction of assembly. In this embodiment, the squared-off tabs 1727 are not surrounded by retaining ring 1725 material. The ring 1725 is also shown with an exemplary lip 1750 for engaging with a recess or a flat surface of a protruding ridge of a chassis component. The ring 1725 is also shown with an exemplary opening 1760 that may allow the ring 1725 to temporarily expand when engaging the protruding ridge.

Figure 18:
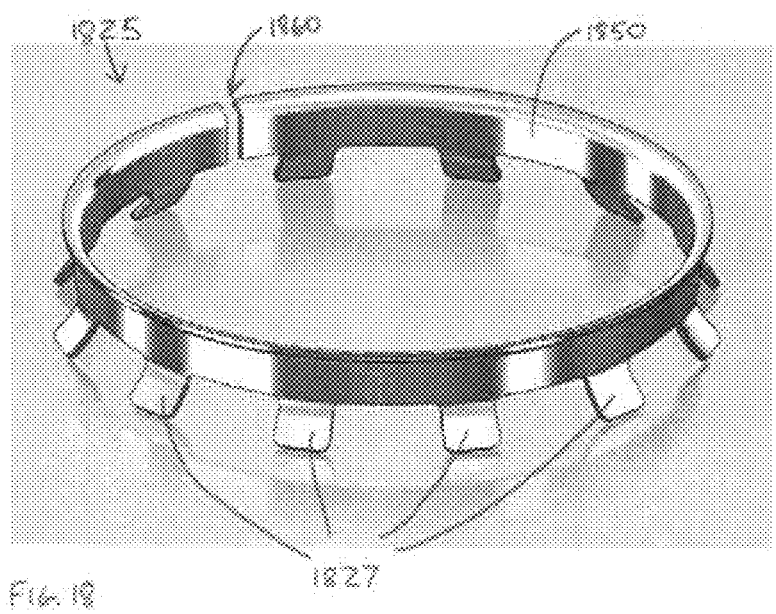

FIG. 18 is a view of another exemplary retaining ring 1825. In this embodiment, tabs 1827 are stamped into the retaining ring 1825 and are biased or bent in the direction of assembly. In this embodiment, the tabs 1827 are not surrounded by retaining ring 1825 material. The ring 1825 is also shown with an exemplary flat surface 1850 for engaging with a recess or a flat surface of a protruding ridge of a chassis component. The ring 1825 is also shown with an exemplary opening 1860 that may allow the ring 1825 to temporarily expand when engaging the protruding ridge.

Figure 19:
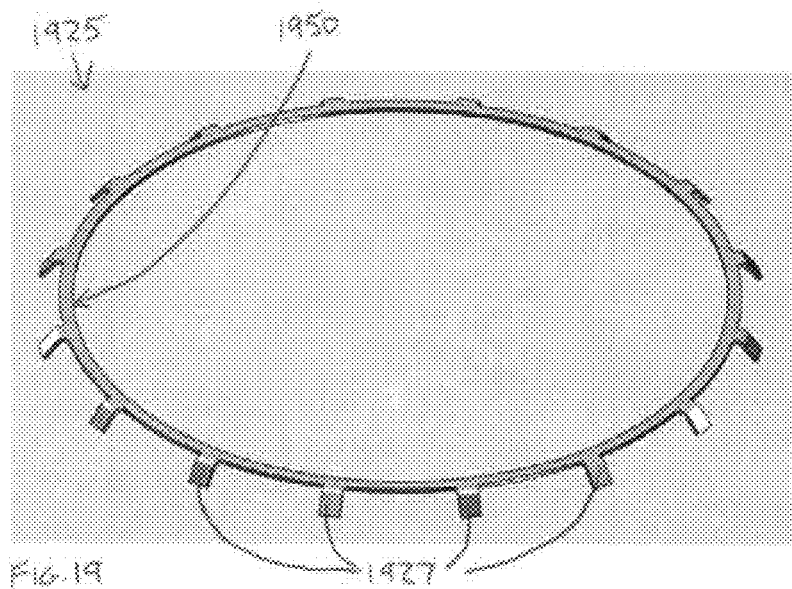

FIG. 19 is a view of another exemplary retaining ring 1925. In this embodiment, tabs 1927 are stamped into the retaining ring 1925 and are biased or bent in the direction of assembly. In this embodiment, the tabs 1927 are not surrounded by retaining ring 1825 material. The ring 1925 is also shown with an exemplary edge 1950 for engaging with a recess or a flat surface of a protruding ridge of a chassis component.

Figure 20:
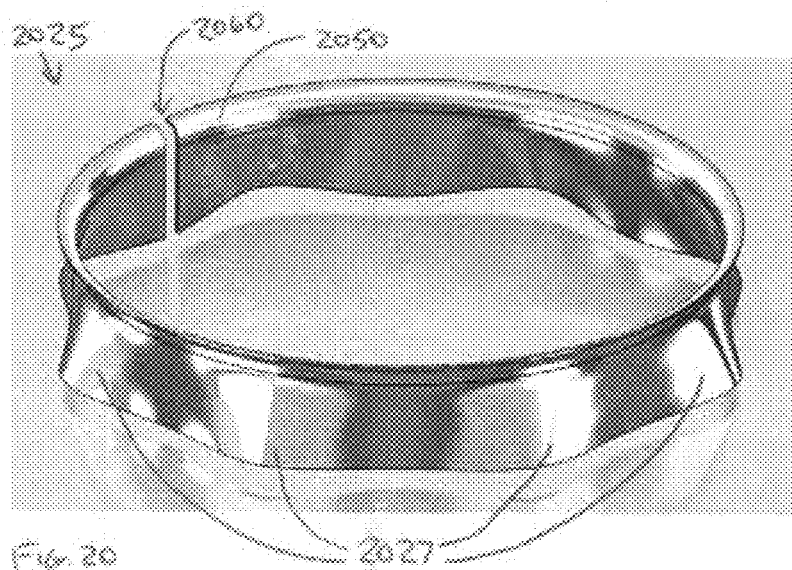

FIG. 20 is a view of another exemplary retaining ring 2025. In this embodiment, wave-like skirt features 2027 are formed into the retaining ring 2025 and are sloped in the direction of assembly. The ring 2025 is also shown with an exemplary ridge 2050 for engaging with a recess or a flat surface of a protruding ridge of a chassis component. The ring 2025 is also shown with an exemplary opening 2060 that may allow the ring 2025 to temporarily expand when engaging the protruding ridge.

Figure 21:
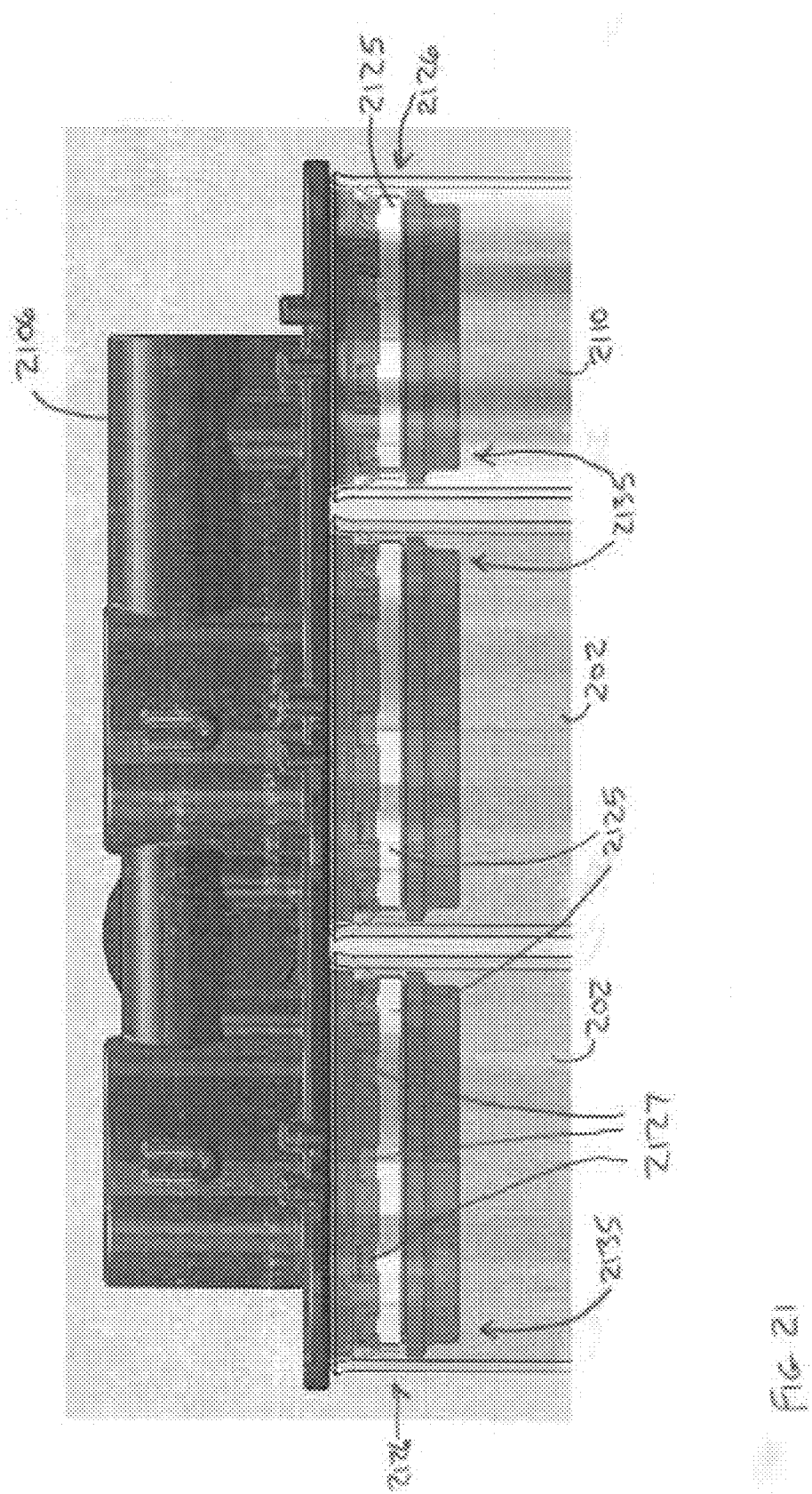
FIG. 21 illustrates one embodiment of two sieve bed vessels and a product tank coupled to a top manifold assembly of an oxygen concentrator.

FIG. 21 is an exploded view of a top manifold assembly 2106, shown coupling with the top end of exemplary sieve bed vessels 202 and product tank 2110. FIG. 21 shows the sieve bed vessels and the product tank after they have been pressed onto the manifold assembly 2106. This embodiment is shown with exemplary retaining rings 2125 and protruding ridges 2135. In this embodiment, the protruding ridge 2135 has a recess 2126 molded into the side of the protruding ridge 2135 to accept the retaining ring 2125. The retaining rings 2125 are shown with a plurality of tabs 2127 to lock the sieve bed vessels 202 and the product tank 2110 to the manifold assembly 2102 during the "press-fit" or "press-together" assembly operation. In this embodiment, the tabs 2127 are stamped into the retaining rings 2125.

The inventive aspects have been described with reference to the exemplary embodiments. Modification and alterations will occur to others upon a reading and understanding of this specification. It is intended to include all such modifications and alterations insofar as they come within the scope of the appended claims or the equivalents thereof.

The invention claimed is:

1. A concentrator for providing a breathing gas comprising:
   at least one sieve bed comprising a vessel containing a gas separation medium;
   a first chassis component, comprising at least one protrusion extending from the first chassis component to couple with a surface of the at least one sieve bed vessel; and
   a first locking element to engage the surface of the at least one sieve bed vessel to lock the coupled vessel to the first chassis component as the vessel and first chassis component are pressed together concentrically along a central axis with an insertion force;
   wherein the protrusion cross-sectional shape and the vessel cross-sectional shape are concentric.

2. The concentrator of claim 1, wherein the at least one protrusion comprises the first locking element.

3. The concentrator of claim 1, wherein the sieve bed vessel comprises the first locking element.

4. The concentrator of claim 1, wherein the at least one protrusion comprises a protrusion cross-sectional shape that mates to a vessel cross-sectional shape of the vessel.

5. The concentrator of claim 4, wherein the insertion force as the vessel and first chassis component are pressed together is less than a removal force to remove the vessel from the first chassis component.

6. The concentrator of claim 1, wherein the at least one protrusion comprises a plurality of protrusions.

7. The concentrator of claim 1, wherein the first locking element engages an inner vessel surface and an outer protrusion surface to couple the at least one sieve bed vessel to the first chassis component.

8. The concentrator of claim 1, wherein the first locking element engages an outer vessel surface and an inner protrusion surface to couple the at least one sieve bed vessel to the first chassis component.

9. The concentrator of claim 1, wherein the first locking element is seated in a first recess of the at least one protrusion.

10. The concentrator of claim 1, wherein the first locking element comprises a first retaining ring, wherein the first retaining ring comprises a ring shape that mates to a vessel cross-sectional shape of the vessel.

11. The concentrator of claim 10, wherein the first retaining ring comprises at least one tab to engage a surface of the vessel to lock the coupled vessel to the first chassis component as the vessel and first chassis component are pressed together along the central axis.

12. The concentrator of claim 1, wherein the first chassis component further comprises a first sealing element to seal the vessel to the first chassis component.

13. The concentrator of claim 12, wherein the at least one protrusion comprises the first sealing element.

14. The concentrator of claim 12, wherein the first sealing element comprises a seal shape that mates to a vessel cross-sectional shape of the vessel.

15. The concentrator of claim 12, wherein the first sealing element engages an inner vessel surface to seal the vessel to the first chassis component.

16. The concentrator of claim 12, wherein the first sealing element is seated in a second recess of the at least one protrusion.

17. The concentrator of claim 1, further comprising:
   at least one product tank, wherein the first chassis component further comprises at least one tank protrusion extending from the first chassis component to couple the at least one product tank to the first chassis component; and a second locking element to lock the coupled tank to the first chassis component.

18. The concentrator of claim 1, further comprising:
a second chassis component, comprising at least one protrusion extending from the second chassis component to couple the at least one sieve bed vessel to the second chassis component; and
a second locking element to lock the coupled vessel to the second chassis component.

19. A chassis component for a gas concentrator, comprising:
at least one protrusion extending from the chassis component to couple with a surface of at least one sieve bed vessel, wherein the at least one sieve bed vessel contains a gas separation medium;
a locking element to engage the surface of the at least one sieve bed vessel to lock the coupled vessel to the first chassis component as the vessel and first chassis component are pressed together concentrically along a central axis with an insertion force; and
a sealing element to seal the coupled vessel to the first chassis component.

20. A concentrator for providing a breathing gas comprising:
a means for containing a gas separation medium;
a means for coupling a chassis component to a surface of the means for containing the gas separation medium; and
a first locking means to engage the surface of the means for containing the gas separation medium to lock the means for coupling the chassis component to the means for containing the gas separation medium as the means for containing the gas separation medium and the chassis component are pressed together concentrically along a central axis with an insertion force.

21. The concentrator of claim 11, wherein the at least one tab is biased in the direction of assembly.

22. A method of assembling a concentrator for providing a breathing gas comprising:
providing at least one sieve bed comprising a vessel containing a gas separation medium;
providing a first chassis component comprising at least one protrusion extending from the first chassis component to couple with a surface of the at least one sieve bed vessel;
providing a first locking element to engage the surface of the at least one sieve bed vessel to lock the coupled vessel to the first chassis component as the vessel and first chassis component are pressed together concentrically along a central axis with an insertion force; and
concentrically pressing together the vessel and first chassis component along the central axis;
wherein the protrusion cross-sectional shape and the vessel cross-sectional shape are concentric.

* * * * *